US011382927B2

(12) United States Patent
Tanisaka et al.

(10) Patent No.: US 11,382,927 B2
(45) Date of Patent: Jul. 12, 2022

(54) LIQUID MEDICINAL PREPARATION

(71) Applicant: FUJIFILM Corporation, Tokyo (JP)

(72) Inventors: Hiroki Tanisaka, Kanagawa (JP); Tatsuya Murakami, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 254 days.

(21) Appl. No.: 16/114,457

(22) Filed: Aug. 28, 2018

(65) Prior Publication Data

US 2018/0360865 A1 Dec. 20, 2018

Related U.S. Application Data

(63) Continuation of application No. PCT/JP2017/007720, filed on Feb. 28, 2017.

(30) Foreign Application Priority Data

Feb. 29, 2016 (JP) .............................. JP2016-037309
Oct. 25, 2016 (JP) .............................. JP2016-208563

(51) Int. Cl.
| | |
|---|---|
| *A61K 31/7068* | (2006.01) |
| *A61K 47/10* | (2017.01) |
| *A61K 9/08* | (2006.01) |
| *A61P 35/00* | (2006.01) |
| *A61K 9/00* | (2006.01) |
| *A61K 47/02* | (2006.01) |
| *A61K 47/26* | (2006.01) |

(52) U.S. Cl.
CPC ........ *A61K 31/7068* (2013.01); *A61K 9/0019* (2013.01); *A61K 9/08* (2013.01); *A61K 47/02* (2013.01); *A61K 47/10* (2013.01); *A61K 47/26* (2013.01); *A61P 35/00* (2018.01)

(58) Field of Classification Search
CPC .... A61K 47/02; A61K 47/26; A61K 31/7068; A61K 47/10; A61K 9/08; A61K 9/0019; A61P 35/00
See application file for complete search history.

(56) References Cited

U.S. PATENT DOCUMENTS

| | | | |
|---|---|---|---|
| 6,147,058 A | 11/2000 | Yoshimura et al. | |
| 9,221,865 B2 | 12/2015 | Nakamura et al. | |
| 9,475,835 B2 * | 10/2016 | Nakamura | A61K 31/7068 |
| 9,896,471 B2 * | 2/2018 | Baba | C07H 19/073 |
| 10,093,645 B2 * | 10/2018 | Nakamura | C07H 23/00 |
| 2015/0011499 A1 | 1/2015 | Baba et al. | |
| 2018/0327377 A1 * | 11/2018 | Nakamura | C07C 47/277 |

FOREIGN PATENT DOCUMENTS

| | | |
|---|---|---|
| CN | 101402662 A | 4/2009 |
| CN | 104203969 A | 12/2014 |
| WO | 97/038001 A1 | 10/1997 |
| WO | 2007/130783 A2 | 11/2007 |
| WO | 2010/132513 A1 | 11/2010 |
| WO | 2011/074484 A1 | 6/2011 |
| WO | 2013/146833 A1 | 10/2013 |
| WO | 2014/027658 A1 | 2/2014 |

OTHER PUBLICATIONS

Office Action dated Jan. 8, 2019 from the Australian Patent Office in counterpart Australian Application No. 2017227280.
Office Action dated Sep. 24, 2019, from the Intellectual Property of India in counterpart Indian application No. 201847032103.
Office Action dated Jun. 7, 2019 in Russian Application No. 2018134180.
Chemical Encyclopaedia edited by N.S. Zefirova, "Bolshaya Rossiyskaya Entsiklopediya" Publishing House, Moscow, 1995, vol. 4, pp. 184 to 189, "Solutions" (7 pages total).
Office Action dated Aug. 2, 2019 from the Australian Patent Office in Australian Application No. 2017227280.
Zajchowski, Deborah A., et al., "Anti-tumor efficacy of the nucleoside analog 1-(2-deoxy-2-fluoro-4-thio-β-D-arabinofuranosyl) cytosine (4'-thio-FAC) in human pancreatic and ovarian tumor xenograft models", Int. J. Cancer, vol. 114, No. 6, pp. 1002-1009, May 10, 2005, 8 pages total.
Extended European Search Report dated Feb. 14, 2019 issued by the European Patent Office in counterpart European application No. 17759977.6.
Office Action dated Sep. 12, 2019, from the Canadian Intellectual Property Office in corresponding Canadian Application No. 3,016,020.
Office Action dated Dec. 19, 2019, from the State Intellectual Property Office of the P.R.C in Chinese Application No. 201780013878.0.
Fude CUI, editor, "Pharmaceutics", People's Medical Publishing House, 7th Edition, Aug. 2011, pp. 23 and 143 (4 pages total).
Takahashi et al., "Synthesis and crystal structure of 2'-deoxy-2'-fluoro-4'-thioribonucleosides: substrates for the synthesis of novel modified RNAs", Science Direct, Tetrahedron, vol. 64, 2008, pp. 4313-4324.
Shinji Miura, et al., "Comparison of 1-(2-deoxy-2-fuoro-4-thio-β-D-arabinofuranosyl)cytosine with gemcitabine in its antitumor activity", Cancer Letters, 1999, pp. 177-182, vol. 144.
Shinji Miura, et al., "Potent antitumor effect of 1-(2-deoxy-2-fluoro-4-thio-β-D-arabinofuranosyl)cytosine on peritoneal dissemination models of gastrointestinal cancers", Oncology Reports, 2002, pp. 1319-1322, vol. 9.
Office Action dated Sep. 25, 2018, from Japanese Patent Office in counterpart Japanese Application No. 2016-208563.

(Continued)

*Primary Examiner* — Layla D Berry
(74) *Attorney, Agent, or Firm* — Sughrue Mion, PLLC

(57) ABSTRACT

An object of the present invention is to provide a liquid medicinal preparation which does not generate precipitates and is suitable for mass production. According to the present invention, provided is a liquid medicinal preparation that contains 1-(2-deoxy-2-fluoro-4-thio-β-D-arabinofuranosyl) cytosine or a salt thereof, a polyhydric alcohol having a molecular weight of 100 or less, and water. The polyhydric alcohol is preferably glycerin, propylene glycol, or butanediol.

9 Claims, No Drawings

(56) References Cited

OTHER PUBLICATIONS

International Search Report dated Mar. 28, 2017 from the International Searching Authority in counterpart International Application No. PCT/JP2017/007720.
International Preliminary Report on Patentability dated Sep. 4, 2018 from the International Bureau in counterpart International Application No. PCT/JP2017/007720.
Written Opinion dated Mar. 28, 2017 from the International Bureau in counterpart International Application No. PCT/JP2017/007720.
Office Action dated Oct. 29, 2020 by the Patent Office of Taiwan in Taiwan application No. 106106284.
Office Action dated Feb. 24, 2021 from the Taiwanese Patent Office in Taiwanese Application No. 106106284.
Office Action dated Aug. 18, 2020, from the State Intellectual Property Office of the P.R.C. in Chinese application No. 201780013878.0.
Office Action dated Aug. 12, 2021 by the Brazilian Patent Office in Brazilian Application No. 112018067808-2.

\* cited by examiner

LIQUID MEDICINAL PREPARATION

CROSS-REFERENCE TO RELATED APPLICATIONS

This application is a Continuation of PCT International Application No. PCT/JP2017/007720 filed on Feb. 28, 2018, which claims priorities under 35 U.S.C. § 119(a) to Japanese Patent Application No. 2016-037309 filed on Feb. 29, 2016 and Japanese Patent Application No. 2016-208563 filed on Oct. 25, 2016. Each of the above application(s) is hereby expressly incorporated by reference, in its entirety, into the present application.

BACKGROUND OF THE INVENTION

1. Field of the Invention

The present invention relates to a liquid medicinal preparation which is useful as an antitumor agent.

2. Description of the Related Art

It is known that 1-(2-deoxy-2-fluoro-4-thio-β-D-arabinofuranosyl)cytosine (hereinafter, sometimes referred to as "Compound A") has an excellent antitumor activity and is useful as a tumor therapeutic agent (WO1997/038001A). It is also known that Compound A ha s a strong antitumor activity even upon oral administration thereof to mice (Cancer Letters, 1997, Vol. 144, pp. 177 to 182 and Oncology Reports, 2002, Vol. 9, pp. 1319 to 1322). Further, a salt of Compound A and a production method thereof are also known (WO2013/146833A, WO2011/074484A, and WO2014/027658A).

SUMMARY OF THE INVENTION

As a dosage form of a pharmaceutical product in a parenteral administration route, a liquid medicinal preparation in which an active ingredient is dissolved in water is very common and is not limited to an antitumor agent, and a wide variety of pharmaceutical products in the form of the liquid medicinal preparation are on the market. Typically; such a liquid medicinal preparation is designed by setting the concentration of an active ingredient to be sufficiently lower than the saturated solubility thereof in water, so that the active ingredient will not be precipitated during the production process and market circulation of the preparation.

However, although a certain compound has a sufficient solubility in water, environmental changes during the production process (for example, local water evaporation) may result in precipitation thereof. Due to the precipitation, the content of the compound may decrease or insoluble foreign matters or insoluble fine particles may be detected, which may result in nonconformity to the standard. The liquid medicinal preparation of Compound A or a salt thereof also has such properties, and in order to stably produce it, establishment of a technique for suppressing such precipitation is required.

Therefore, an object of the present invention is to provide a liquid medicinal preparation which does not generate precipitates during the production process and is suitable for mass production.

As a result of investigating various additives, the present inventors have found that addition of a polyhydric alcohol having a molecular weight of 100 or less contributes to the provision of a liquid medicinal preparation which does not generate precipitates and is suitable for mass production. The present invention has been completed based on these findings. It is presumed that the generation of precipitates can be sufficiently suppressed in the mass production process because, by adding a polyhydric alcohol having a molecular weight of 100 or less, the supersaturation time of Compound A can be delayed even in the case where local water evaporation occurs, and the stability of the preparation can be increased.

The present invention provides the following.

A liquid medicinal preparation, comprising:
1-(2-deoxy-2-fluoro-4-thio-β-D-arabinofuranosyl)cytosine or a salt thereof;
a polyhydric alcohol having a molecular weight of 100 or less; and
water.

The polyhydric alcohol is preferably a polyhydric alcohol having 3 or 4 carbon atoms, more preferably glycerin, propylene glycol, or butanediol, and particularly preferably glycerin. The content of the polyhydric alcohol is preferably 0.5% to 10% by mass, and more preferably 0.5% to 5% by mass.

The pH of the liquid medicinal preparation is preferably 1.5 to 6.9, more preferably 1.5 to 6.5, still more preferably 2.0 to 6.5, and particularly preferably 2.0 to 4.0.

The content of 1-(2-deoxy-2-fluoro-4-thio-β-D-arabinofuranosyl)cytosine or a salt thereof is preferably 1 to 50 mg/mL.

The salt of 1-(2-deoxy-2-fluoro-4-thio-β-D-arabinofuranosyl)cytosine is preferably a methanesulfonate, hydrochloride, ½ sulfate, nitrate, or hydroiodide of 1-(2-deoxy-2-fluoro-4-thio-β-D-arabinofuranosyl)cytosine.

The liquid medicinal preparation is preferably a solution injection, and is preferably used for the treatment of a tumor.

The present invention further provides the following.

A method for the treatment of a tumor, comprising a step of administering the liquid medicinal preparation to a subject (a mammal including a human, and preferably a human).

The liquid medicinal preparation, which is for use in a method for the treatment of a tumor, or which is for an antitumor agent.

In the present invention, the "treatment" includes prevention and therapy.

According to the present invention, it is possible to provide a liquid medicinal preparation which does not generate precipitates during the production process and is suitable for mass production.

DESCRIPTION OF THE PREFERRED EMBODIMENTS

Hereinafter, the present invention will be described in detail. In the present invention, the numerical value represented by "%" is based on the mass, unless otherwise specified, and the range represented by "to" includes the values at both ends, unless otherwise specified.

The present invention relates to a liquid medicinal preparation including 1-(2-deoxy-2-fluoro-4-thio-β-D-arabinofuranosyl)cytosine (Compound A) or a pharmaceutically acceptable salt thereof (hereinafter, sometimes referred to as "salt thereof"), a polyhydric alcohol having a molecular weight of 100 or less, and water.

First, Compound A or a salt thereof will be described.

Examples of the salt include a mineral acid salt, organic carboxylate, and sulfonate. Preferred examples of the salt include a mineral acid salt and sulfonate.

Examples of the mineral acid salt include hydrochloride, hydrobromide, hydroiodide, nitrate, phosphate, and sulfate, among which hydrochloride, hydroiodide, nitrate, or sulfate is preferred, and hydrochloride is more preferred. Examples of the organic carboxylate include formate, acetate, citrate, oxalate, fumarate, maleate, succinate, malate, tartarate, aspartate, trichloroacetate, and trifluoroacetate. Examples of the sulfonate include methanesulfonate, benzenesulfonate, p-toluenesulfonate, mesitylenesulfonate, and naphthalenesulfonate, among Which methanesulfonate is preferred.

The salt of Compound A may be an anhydride, a hydrate, or a solvate. In the ease of being merely referred to as "salt" herein, its form may be an anhydride, a hydrate, or a solvate. In the present specification, the term "anhydride" refers to a state where the form is not a hydrate or a solvate, unless otherwise specified. Even a substance which does not form a hydrate or a solvate originally is included in the "anhydride" referred to in the present invention as long as it does not have water of crystallization, water of hydration, and a solvent which interacts therewith. The anhydride may also be referred to as "nonhydrate". In the case where it is a hydrate, the number of water molecules in the hydrate is not particularly limited and the hydrate may be monohydrate, dihydrate, or the like. Examples of the solvate include methanolates, ethanolates, propanolates, and 2-propanolates.

Specific examples of particularly preferred salts of Compound A are as follows.

Methanesulfonate of 1-(2-deoxy-2-fluoro-4-thio-β-D-arabinofuranosyl)cytosine;

Hydrochloride of 1-(2-deoxy-2-fluoro-4-thio-β-D-arabinofuranosyl)cytosine;

½ sulfate of 1-(2-deoxy-2-fluoro-4-thio-β-D-arabinofuranosyl)cytosine;

Nitrate of 1-(2-deoxy-2-fluoro-4-thio-β-D-arabinofuranosyl)cytosine;

Hydroiodide of 1-(2-deoxy-2-fluoro-4-thio-β-D-arabinofuranosyl)cytosine; and an anhydride of any of the above salts.

The salt of Compound A may be a crystal. One preferred aspect thereof is a methanesulfonate crystal of 1-(2-deoxy-2-fluoro-4-thio-β-D-arabinofuranosyl)cytosine having characteristic peaks at 19.8°, 21.8°, 27.5°; 28.4° and 29.9° in terms of a diffraction angle (2θ) by powder X-ray diffraction. Another preferred example is a hydrochloride crystal of 1-(2-deoxy-2-fluoro-4-thio-β-D-arabinofuranosyl)cytosine having characteristic peaks at 9.2°, 14.7°, 15.7°, 22.9° and 27.3° in terms of a diffraction angle (2θ) by powder X-ray diffraction. Note that the characteristic peaks due to powder X-ray diffraction of crystals may vary depending on measurement conditions. Generally, an error occurs within the range of 2θ±0.2°. Therefore, in the present invention, unless otherwise specified, in the case of referring to the "diffraction angle of X° represented by 2θ", it means a "diffraction angle of ((X−0.2) to (X+0.2))° represented by 2θ". Therefore, the present invention includes not only a crystal in which the diffraction angles in powder X-ray diffraction completely coincide but also a crystal in which the diffraction angle coincides within an error range of +0.2°.

The liquid medicinal preparation of the present invention may employ only one type or two or more types of Compound A and various salts thereof.

The content of Compound A or a salt thereof in the liquid medicinal preparation is preferably 1 to 50 mg/mL, more preferably 5 to 50 mg/mL, and particularly preferably 10 to 30 mg/mL. In terms of content as Compound A or a salt thereof, 5 to 50 mg/mL is 0.5% to 5% by mass, and 10 to 30 mg/mL is 1% to 3% by mass. The content may be set to a sufficient amount to ensure the medicinal effect of the liquid medicinal preparation. In the case where the content is less than the above-specified lower limit value, there is a possibility that the medicinal effect becomes insufficient. On the other hand, in the case where the content exceeds the above-specified upper limit value, the precipitates of Compound A may be generated due to environmental changes in the production process of the preparation.

Next, a method for producing Compound A or a salt thereof will be described. Compound A can be produced by the method described in WO1997/038001A and Journal of Organic Chemistry, 1999, Vol. 64, pp. 7912 to 7920. The salt of Compound A or a hydrate or solvate thereof can be produced by the method described in WO2014/027658A.

Compound A and the salt thereof according to the present invention can be used as an antitumor agent or as an active ingredient of a pharmaceutical composition.

Next, a polyhydric alcohol having a molecular weight of 100 or less will be described.

The polyhydric alcohol having a molecular weight of 100 or less is preferably a polyhydric alcohol having 3 or 4 carbon atoms, more preferably glycerin, propylene glycol, or butanediol, and particularly preferably glycerin. Examples of butanediol include 1,2-butanediol, 1,3-butanediol, 1,4-butanediol, and 2,3-butanediol, among which 1,3-butanediol is particularly preferred. The lower limit of the molecular weight of the polyhydric alcohol is not particularly limited, but it is generally 50 or more.

The content of the polyhydric alcohol having a molecular weight of 100 or less in the liquid medicinal preparation is preferably 0.5% to 10% by mass, more preferably 0.5% to 5% by mass, and still more preferably 1.0% to 2.5% by mass. The content of the polyhydric alcohol may be used in an amount sufficient to suppress the precipitation of Compound A in the production process of the preparation. In the case of the above-specified content of the polyhydric alcohol, the precipitation of Compound A can be suppressed more sufficiently, the preparation stability is excellent, and the generation of the precipitates of Compound A can be suppressed even in the case of being stored for a long period of time in refrigeration. In the case where the content of the polyhydric alcohol is high, an osmotic pressure increases, so there is a concern that patients who develop phlebitis may occur, which makes handling of injections sometimes difficult. The content of the polyhydric alcohol is preferably 0.5% to 5% by mass from the viewpoint of suppressing precipitation and adjusting to an appropriate osmotic pressure in the production process of the liquid medicinal preparation.

Next, water will be described. Usually; sterile water, preferably pyrogen-free sterile water, is used as water.

The liquid medicinal preparation of the present invention may contain, in addition to the above-mentioned ingredients, an additive such as a pH adjusting agent, a flavoring agent, an emulsifying agent, a surfactant, a solubilizing agent, a suspending agent, a tonicity agent, a buffering agent, a preservative, an antioxidant, a stabilizer, or an absorption accelerator. The content of the additive is preferably 0.001% to 10% by mass, more preferably 0.001% to 5% by mass, and still more preferably 0.001% to 2% by mass.

A variety of commonly used pH adjusting agents can be used as the pH adjusting agent. Specific examples thereof include potassium hydroxide, calcium hydroxide, sodium hydroxide, magnesium hydroxide, monoethanolamine, diethanolamine, triethanolamine, ammonia, hydrochloric acid, methanesulfonic acid, sulfuric acid, nitric acid, and hydroiodic acid. Among them, sodium hydroxide, hydrochloric acid, methanesulfonic acid, or a combination of hydrochloric acid and sodium hydroxide is preferable.

The content of the pH adjusting agent is set so that the liquid medicinal preparation has a desired pH depending on the type and content of Compound A and a salt thereof.

The liquid medicinal preparation of the present invention preferably has a pH of 1.5 to 6.9, more preferably 1.5 to 6.5, still more preferably 2.0 to 6.5, even still more preferably 2.0 to 5.0, still further preferably 2.0 to 4.0, particularly preferably 2.6 to 3.2, and most preferably 2.8 to 3.0. In the case where the pH of the liquid medicinal preparation is high, the solubility of Compound A or a salt thereof becomes lower, so a pH within the above-specified range is preferable for mass production of the preparation.

The liquid medicinal preparation of the present invention preferably contains Compound A or a salt thereof, a polyhydric alcohol having a molecular weight of 100 or less, and water, and optionally contains a pH adjusting agent.

The content of water is used in an amount of 100% by mass in total with the ingredients contained in the preparation such as Compound A or a salt thereof, a polyhydric alcohol having a molecular weight of 100 or less, and additives. Specifically, the content of water is preferably 80% by mass or more, and more preferably 90% by mass or more.

The liquid medicinal preparation of the present invention can be produced by a conventional method. For example, first, ingredients (hereinafter, referred to as included ingredients) contained in the liquid medicinal preparation of the present invention are dissolved in water. The mixing order of the included ingredients is not particularly limited, and all of the included ingredients may be mixed at the same time, or only a part of the included ingredients may be dissolved first in water, and then the remaining included ingredients may be dissolved.

More specifically, Compound A or a salt thereof as a raw material is dissolved in water in which a polyhydric alcohol having a molecular weight of 100 or less is dissolved. Thereafter, pH is adjusted by adding a pH adjusting agent.

In the case where Compound A is used as a raw material, it is preferable to use sodium hydroxide and methanesulfonic acid, hydrochloric acid, sulfuric acid, nitric acid, or hydroiodic acid as a pH adjusting agent. By using methanesulfonic acid, hydrochloric acid, sulfuric acid, nitric acid, or hydroiodic acid, the precipitation of Compound A can be sufficiently suppressed in the production process of the preparation.

A liquid medicinal preparation obtained by using a salt of Compound A as a raw material can be interpreted as containing a salt of Compound A in the present specification.

Then, the obtained solution is subjected to a heat sterilization treatment by filter sterilization with a membrane filter, pressurized heat sterilization by an autoclave, intermittent sterilization method, or the like.

The liquid medicinal preparation (the foregoing solution) of the present invention is filled in a container suitable for storage of a medicinal preparation, such as an ampoule, a vial, or a syringe, by using a pump. In the case where a liquid medicinal preparation is administered, the liquid medicinal preparation is added to an infusion solution such as physiological saline or glucose solution and then administered to a patient.

The liquid medicinal preparation of the present invention can be used for the treatment of tumors. The liquid medicinal preparation of the present invention can be effectively used for the treatment of melanoma, liver cancer, glioma, neuroblastoma, sarcoma, and various types of tumors including tumors of the lung, the colon, the breast, the bladder, the ovary, the testis, the prostate, the cervix, the pancreas, the stomach, the small intestine, and other organs. The liquid medicinal preparation of the present invention is particularly effective for the treatment of pancreatic cancer. The preparation of the present invention may be used in combination with other therapeutic agents including known antitumor agents conventionally used in the art.

The administration route of the liquid medicinal preparation of the present invention includes, for example, intravenous, intraarterial, intrarectal, intraperitoneal, intramuscular, intratumoral, or intravesical injection, Examples of dosage forms of the liquid medicinal preparation include injections.

EXAMPLES

Hereinafter, the present invention will be described with reference to Examples and Comparative Examples, but the present invention is not limited thereto.

<Evaluation Method>

(1) Evaluation of Precipitation

Each of the liquid medicinal preparations of Examples and Comparative Examples was dispensed in an amount of 0.8 mL/well into a 12-well plate. This was allowed to stand in a draft chamber (L7R18CSP-ZA, manufactured by Okamura Corporation) at a temperature of about 25° C. and a humidity of 50% RH (relative humidity), and the state was observed. The time until the white solid ingredient of Compound A precipitated on the wall or the bottom of each well (precipitation starting time) was recorded. The difference between the precipitation starting time of Comparative Example 1 and the precipitation starting time of Examples 1 to 39 and Comparative Examples 2 to 10 was calculated as the precipitation delay time. In the case where the precipitation delay time is 0.5 hours or longer, it is assumed that there is a precipitation delay effect. In the table below, those having a precipitation delay effect are described as A, and those having no precipitation delay effect are described as B.

(2) Evaluation of Preparation Stability 3 mL of each of the liquid medicinal preparations of Examples and Comparative Examples was filled in a glass vial and sealed tightly. This was stored at a constant temperature of 60° C. for one week. Samples before and after storage thereof were analyzed by high performance liquid chromatography (HPLC) under the following measurement conditions. Each chromatogram thus obtained was compared and the relative retention time and yield of unknown related substance produced after storage compared to before storage were recorded. The unknown related substance refers to a substance corresponding to a newly generated peak as compared with the chromatogram after storage in Comparative Example 1.

<HPLC Measurement Conditions>

Column: ACQUITY UPLC HSS T 3, 1.8 µm (2.1 mm×150 mm)

Column temperature: 22° C.

Mobile phase A: 0.1% trifluoroacetic acid (TFA), water

Mobile phase B: 0.1% TEA, acetonitrile/water=9/1

Flow rate: 0.3 mL/min

Gradient: 0 min (B 3%)→9 min (B 3%)→19 min (B 65%)→23 min (B 65%)→23.1 min (B 3%)→33 min (B 3%)

Detector wavelength: 280 nm (3) Saturated Solubility

The saturated solubility of Compound A was determined at the same content of additives and pH as those of the liquid medicinal preparations of Examples and Comparative Examples. That is, saturated solutions of Compound A were prepared by adding an excessive amount of methanesulfonate or hydrochloride of Compound A and sodium hydroxide to adjust the pH to the liquid medicinal preparations of Examples and Comparative Examples. With respect to the liquids obtained by removing undissolved Compound A from these saturated solutions, the content of Compound A was quantified by HPLC and calculated as saturated solubility.

(4) Osmotic Pressure Ratio

With respect to the liquid medicinal preparations of Examples and Comparative Examples, an osmotic pressure was measured using an osmometer (OSMOMAT 030, manufactured by Gonotec GmbH), and the ratio of osmotic pressure to physiological saline was calculated. The osmotic pressure ratio is preferably close to 1. In the case where the osmotic pressure ratio becomes higher, phlebitis may occur by injection administration, so it is preferable to set the osmotic pressure ratio to 3 or less.

Preparation of Methanesulfonate of Compound A

Compound A was prepared by the method described in Journal of Organic Chemistry, 1999, Vol. 64. pp. 7912 to 7920. Methanesulfonic acid (0.99 mL) was added to a suspension of Compound A (4.0 g) in water (73 mL), and the mixture was stirred at room temperature for 35 minutes. After confirming the dissolution by visual observation, the solvent was distilled off under reduced pressure. Acetone (75 mL) was added to the resulting residue which was then stirred at room temperature for 30 minutes. The solid was collected by filtration, washed with acetone and blast-dried to obtain methanesulfonate (5.2 g) of Compound A as a white solid.

Liquid pharmaceutical compositions of the following Examples and Comparative Examples were prepared, and evaluation of precipitation and evaluation of preparation stability were carried out in accordance with the foregoing method to measure the saturated solubility and osmotic pressure ratio. The obtained results are shown in the following table.

EXAMPLES AND COMPARATIVE EXAMPLES

Comparative Example 1

The methanesulfonate of Compound A was dissolved in an appropriate amount of water for injection and the pH was adjusted with a 1 mol/L sodium hydroxide aqueous solution. An appropriate amount of water for injection was added and mixed so that the concentration of Compound A was 20 mg/mL. This liquid was filtered through a membrane filter (0.22 μm) to obtain a liquid medicinal preparation of Comparative Example 1 shown in the following table.

Examples 1 to 6

Liquid medicinal preparations of Examples 1 to 6 were obtained in the same manner as in Comparative Example 1, except that glycerin (manufactured by Merck & Co., Inc.) was added at the concentration shown in the following table.

Examples 7 and 8

Liquid medicinal preparations of Examples 7 and 8 were obtained in the same manner as in Example 3, except that the pH was changed by adjusting the additive amount of a 1 mol/L sodium hydroxide aqueous solution.

Examples 9 to 13

Liquid medicinal preparations of Examples 9 to 13 were obtained in the same manner as in Comparative Example 1, except that propylene glycol (manufactured by J. T. Baker Chemical Company) was added at the concentration shown in the following table.

Example 14

A liquid medicinal preparation of Example 14 was obtained in the same manner as in Comparative Example 1, except that 1,3-butanediol (manufactured by Daicel Corporation) was added at the concentration shown in the following table.

Comparative Examples 2 to 9

Liquid medicinal preparations of Comparative Examples 2 to 9 were obtained in the same manner as in Comparative Example 1, except that the additives shown in the following table were added at the concentrations shown in the following table.

Examples 15 to 19

Liquid medicinal preparations of Examples 15 to 19 were obtained in the same manner as in Example 3, except that the additive amount of methanesulfonate of Compound A was changed to the concentration of Compound A shown in the following table.

Example 20

A liquid medicinal preparation of Example 20 was obtained in the same manner as in Example 3, except that the hydrochloride of Compound A was used in place of the methanesulfonate of Compound A.

Comparative Example 10

A liquid medicinal preparation of Comparative Example 10 was obtained in the same manner as in Comparative Example 1, except that Compound A was used in place of the methanesulfonate of Compound A, and further, glucose was added at the concentration shown in the following table. This preparation was the same as Preparation Example 3 in Examples of WO1997/038001A.

Examples 21 and 22

Liquid medicinal preparations of Examples 21 and 22 were obtained in the same manner as in Example 3, except that the was changed by adjusting the additive amount of a 1 mol/L sodium hydroxide aqueous solution.

Example 23

A liquid medicinal preparation of Example 23 was obtained in the same manner as in Example 3, except that Compound A was used in place of the methanesulfonate of Compound A and the pH was adjusted using methanesulfonic acid and a 1 mol/L sodium hydroxide aqueous solution in place of the 1 mol/L sodium hydroxide aqueous solution.

Example 24

A liquid medicinal preparation of Example 24 was obtained in the same manner as in Example 23, except that Compound A was used in place of the methanesulfonate of Compound A and the pH was adjusted using hydrochloric acid in place of methanesulfonic acid.

Examples 25 to 29

Liquid medicinal preparations of Examples 25 to 29 were obtained in the same manner as in Example 3, except that the additive amount of the methanesulfonate of Compound A was changed to the concentration of Compound A shown in the following table and the pH was changed by adjusting the additive amount of a 1 mol/L sodium hydroxide aqueous solution.

Examples 30 to 37

Liquid medicinal preparations of Examples 30 to 37 were obtained in the same manner as in Example 25, except that Compound A was used in place of the methanesulfonate of Compound A and the pH was adjusted using hydrochloric acid and a 1 mat sodium hydroxide aqueous solution in place of the 1 mol/L, sodium hydroxide aqueous solution.

Examples 38 and 39

Liquid medicinal preparations of Examples 38 and 39 were obtained in the same manner as in Example 20, except that glycerin (manufactured by Merck & Co., Inc.) was added at the concentration shown in the following table.

TABLE 1

| | Compound A or salt thereof | Concentration of Compound A (mg/mL) | Additive Product name | Molecular weight | Concentration | Appearance of preparation |
|---|---|---|---|---|---|---|
| Comparative Example 1 | Methanesulfonate of Compound A | 20 | Absent | — | 0% | Homogeneous and clear |
| Example 1 | Methanesulfonate of Compound A | 20 | Glycerin | 92.09 | 0.5% | Homogeneous and clear |
| Example 2 | Methanesulfonate of Compound A | 20 | Glycerin | 92.09 | 1.0% | Homogeneous and clear |
| Example 3 | Methanesulfonate of Compound A | 20 | Glycerin | 92.09 | 1.5% | Homogeneous and clear |
| Example 4 | Methanesulfonate of Compound A | 20 | Glycerin | 92.09 | 2.5% | Homogeneous and clear |
| Example 5 | Methanesulfonate of Compound A | 20 | Glycerin | 92.09 | 5.0% | Homogeneous and clear |
| Example 6 | Methanesulfonate of Compound A | 20 | Glycerin | 92.09 | 10% | Homogeneous and clear |
| Example 7 | Methanesulfonate of Compound A | 20 | Glycerin | 92.09 | 1.5% | Homogeneous and clear |
| Example 8 | Methanesulfonate of Compound A | 20 | Glycerin | 92.09 | 1.5% | Homogeneous and clear |
| Example 9 | Methanesulfonate of Compound A | 20 | Propylene glycol | 76.09 | 0.5% | Homogeneous and clear |
| Example 10 | Methanesulfonate of Compound A | 20 | Propylene glycol | 76.09 | 1.0% | Homogeneous and clear |
| Example 11 | Methanesulfonate of Compound A | 20 | Propylene glycol | 76.09 | 1.5% | Homogeneous and clear |
| Example 12 | Methanesulfonate of Compound A | 20 | Propylene glycol | 76.09 | 2.5% | Homogeneous and clear |
| Example 13 | Methanesulfonate of Compound A | 20 | Propylene glycol | 76.09 | 5.0% | Homogeneous and clear |
| Example 14 | Methanesulfonate of Compound A | 20 | 1,3-Butanediol | 90.12 | 1.5% | Homogeneous and clear |
| Comparative Example 2 | Methanesulfonate of Compound A | 20 | PEG 300 | average of 300 | 1.5% | Homogeneous and clear |
| Comparative Example 3 | Methanesulfonate of Compound A | 20 | PEG 400 | average of 400 | 1.5% | Homogeneous and clear |
| Comparative Example 4 | Methanesulfonate of Compound A | 20 | Glucose | 180.16 | 1.5% | Homogeneous and clear |
| Comparative Example 5 | Methanesulfonate of Compound A | 20 | Fructose | 180.16 | 1.5% | Homogeneous and clear |
| Comparative Example 6 | Methanesulfonate of Compound A | 20 | Lactose hydrate | 342.3 | 1.5% | Homogeneous and clear |
| Comparative Example 7 | Methanesulfonate of Compound A | 20 | D-mannitol | 182.17 | 1.5% | Homogeneous and clear |
| Comparative Example 8 | Methanesulfonate of Compound A | 20 | D-sorbitol | 182.17 | 1.5% | Homogeneous and clear |
| Comparative Example 9 | Methanesulfonate of Compound A | 20 | NaCl | 54.44 | 1.5% | Homogeneous and clear |

TABLE 1-continued

| | | | | | | |
|---|---|---|---|---|---|---|
| Example 15 | Methanesulfonate of Compound A | 5 | Glycerin | 92.09 | 1.5% | Homogeneous and clear |
| Example 16 | Methanesulfonate of Compound A | 10 | Glycerin | 92.09 | 1.5% | Homogeneous and clear |
| Example 17 | Methanesulfonate of Compound A | 30 | Glycerin | 92.09 | 1.5% | Homogeneous and clear |
| Example 18 | Methanesulfonate of Compound A | 40 | Glycerin | 92.09 | 1.5% | Homogeneous and clear |
| Example 19 | Methanesulfonate of Compound A | 50 | Glycerin | 92.09 | 1.5% | Homogeneous and clear |
| Example 20 | Hydrochloride of Compound A | 20 | Glycerin | 92.09 | 1.5% | Homogeneous and clear |
| Comparative Example 10 | Compound A | 30 | Glucose | 180.16 | 10% | Suspension (not dissolved) |
| Example 21 | Methanesulfonate of Compound A | 20 | Glycerin | 92.09 | 1.5% | Homogeneous and clear |
| Example 22 | Methanesulfonate of Compound A | 20 | Glycerin | 92.09 | 1.5% | Homogeneous and clear |
| Example 23 | Compound A | 20 | Glycerin | 92.09 | 1.5% | Homogeneous and clear |
| Example 24 | Compound A | 20 | Glycerin | 92.09 | 1.5% | Homogeneous and clear |
| Example 25 | Methanesulfonate of Compound A | 2 | Glycerin | 92.09 | 1.5% | Homogeneous and clear |
| Example 26 | Methanesulfonate of Compound A | 2 | Glycerin | 92.09 | 1.5% | Homogeneous and clear |
| Example 27 | Methanesulfonate of Compound A | 2 | Glycerin | 92.09 | 1.5% | Homogeneous and clear |
| Example 28 | Methanesulfonate of Compound A | 2 | Glycerin | 92.09 | 1.5% | Homogeneous and clear |
| Example 29 | Methanesulfonate of Compound A | 2 | Glycerin | 92.09 | 1.5% | Homogeneous and clear |
| Example 30 | Compound A | 2 | Glycerin | 92.09 | 1.5% | Homogeneous and clear |
| Example 31 | Compound A | 2 | Glycerin | 92.09 | 1.5% | Homogeneous and clear |
| Example 32 | Compound A | 2 | Glycerin | 92.09 | 1.5% | Homogeneous and clear |
| Example 33 | Compound A | 2 | Glycerin | 92.09 | 1.5% | Homogeneous and clear |
| Example 34 | Compound A | 2 | Glycerin | 92.09 | 1.5% | Homogeneous and clear |
| Example 35 | Compound A | 2 | Glycerin | 92.09 | 1.5% | Homogeneous and clear |
| Example 36 | Compound A | 2 | Glycerin | 92.09 | 1.5% | Homogeneous and clear |
| Example 37 | Compound A | 2 | Glycerin | 92.09 | 1.5% | Homogeneous and clear |
| Example 38 | Hydrochloride of Compound A | 20 | Glycerin | 92.09 | 1.0% | Homogeneous and clear |
| Example 39 | Hydrochloride of Compound A | 20 | Glycerin | 92.09 | 2.5% | Homogeneous and clear |

| | | Evaluation of precipitation | | | | |
|---|---|---|---|---|---|---|
| | pH | Precipitation delay time (hour) | Precipitation delay effect | Evaluation of preparation stability | Saturated solubility mg/mL | Osmotic pressure ratio |
| Comparative Example 1 | 2.9 | 0 | B | n.d. | 75 | 0.5 |
| Example 1 | 2.9 | 0.5 | A | n.d. | 77 | 0.7 |
| Example 2 | 2.9 | 1.0 | A | n.d. | 76 | 0.9 |
| Example 3 | 2.9 | 1.0 | A | n.d. | 74 | 1.1 |
| Example 4 | 2.9 | 1.5 | A | n.d. | 75 | 1.5 |
| Example 5 | 2.9 | >4 | A | n.d. | 75 | 2.6 |
| Example 6 | 2.9 | >4 | A | N.T. | N.T. | 5.1 |
| Example 7 | 2.6 | 1.0 | A | N.T. | N.T. | 1.0 |
| Example 8 | 3.2 | 0.5 | A | N.T. | N.T. | 1.1 |
| Example 9 | 2.9 | 0.5 | A | n.d. | 72 | 0.7 |
| Example 10 | 2.8 | 0.5 | A | n.d. | 73 | 1.0 |
| Example 11 | 2.8 | 1.0 | A | n.d. | 73 | 1.2 |
| Example 12 | 2.8 | 2.0 | A | n.d. | 72 | 1.7 |
| Example 13 | 2.9 | >4 | A | n.d. | 73 | 3.1 |
| Example 14 | 2.9 | 0.5 | A | n.d. | 74 | 1.1 |

TABLE 1-continued

| | | | | | | |
|---|---|---|---|---|---|---|
| Comparative Example 2 | 2.9 | 0 | B | RRT0.22 (0.026%) RRT0.25 (0.035%) | 73 | 0.7 |
| Comparative Example 3 | 2.9 | 0 | B | RRT0.22 (0.040%) RRT0.25 (0.054%) | 74 | 0.6 |
| Comparative Example 4 | 2.9 | 0 | B | RRT0.55 (0.079%) RRT0.74 (0.035%) | 73 | 0.8 |
| Comparative Example 5 | 2.9 | 0 | B | RRT0.97 (0.159%) RRT1.32 (0.073%) | 71 | 0.8 |
| Comparative Example 6 | 2.9 | 0 | B | RRT0.52 (0.019%) RRT0.56 (0.031%) | 72 | 0.6 |
| Comparative Example 7 | 2.9 | 0 | B | n.d. | 72 | 0.8 |
| Comparative Example 8 | 2.9 | 0 | B | n.d. | 72 | 0.8 |
| Comparative Example 9 | 2.8 | 0 | B | n.d. | 57 | 2.2 |
| Example 15 | 2.9 | 4.0 | A | N.T. | N.T. | 0.7 |
| Example 16 | 2.9 | 1.5 | A | N.T. | N.T. | 0.8 |
| Example 17 | 2.9 | 0.5 | A | N.T. | N.T. | 1.3 |
| Example 18 | 2.9 | 0.5 | A | N.T. | N.T. | 1.5 |
| Example 19 | 2.9 | 0.5 | A | N.T. | N.T. | 1.8 |
| Example 20 | 2.9 | 1.0 | A | n.d. | 55 | 1.1 |
| Comparative Example 10 | 6.9 | N.T. | N.T. | N.T. | N.T. | N.T. |
| Example 21 | 1.5 | 2.0 | A | n.d. | N.T. | 1.3 |
| Example 22 | 2.0 | 1.5 | A | n.d. | N.T. | 1.2 |
| Example 23 | 2.9 | 1.0 | A | n.d. | N.T. | 1.1 |
| Example 24 | 2.9 | 1.0 | A | n.d. | N.T. | 1.1 |
| Example 25 | 2.9 | 4.5 | A | n.d. | N.T. | 0.6 |
| Example 26 | 4.0 | 4.5 | A | n.d. | N.T. | 0.7 |
| Example 27 | 6.0 | 4.5 | A | RRT0.82 (0.028%) | N.T. | 0.7 |
| Example 28 | 6.5 | 4.5 | A | RRT0.82 (0.031%) | N.T. | 0.7 |
| Example 29 | 6.9 | 4.5 | A | RRT0.82 (0.032%) | N.T. | 0.7 |
| Example 30 | 1.5 | 4.5 | A | n.d. | N.T. | 0.8 |
| Example 31 | 2.0 | 4.5 | A | n.d. | N.T. | 0.7 |
| Example 32 | 2.6 | 4.5 | A | n.d. | N.T. | 0.6 |
| Example 33 | 3.2 | 0.5 | A | n.d. | N.T. | 0.6 |
| Example 34 | 4.0 | 0.5 | A | n.d. | N.T. | 0.6 |
| Example 35 | 6.0 | 4.5 | A | RRT0.21 (0.021%) RRT0.82 (0.023%) | N.T. | 0.6 |
| Example 36 | 6.5 | 4.5 | A | RRT0.21 (0.023%) RRT0.82 (0.025%) | N.T. | 0.6 |
| Example 37 | 6.9 | 4.5 | A | RRT0.21 (0.030%) RRT0.82 (0.023%) RRT0.88 (0.026%) | N.T. | 0.6 |
| Example 38 | 2.9 | 1.0 | A | n.d. | N.T. | 0.9 |
| Example 39 | 2.9 | 2.0 | A | n.d. | N.T. | 1.5 |

Description of the symbols in the tables: n.d. = not detected. N.T. = not tested.
PEG represents polyethylene glycol.
RRT represents the relative retention time. RRT0.22, RRT0.25, RRT0.55, RRT0.74, RRT0.97, RRT1.32, RRT0.52, RRT0.56, RRT0.82, RRT0.21, and RRT0.88 represent the relative retention times of unknown related substances, respectively.

As can be seen from the above results, the liquid medicinal preparation of the present invention is less likely to exhibit the precipitation of Compound A as compared with Comparative Example 1. In addition, as shown in Comparative Examples 2 to 9, even in the case where a compound which is not a polyhydric alcohol having a molecular weight of 100 or less was added, the evaluation of precipitation was equivalent to Comparative Example 1 in which nothing was added. Further, since unknown related substances may be formed, a compound which is not a polyhydric alcohol having a molecular weight of 100 or less was found to be undesirable as an additive. The evaluation of precipitation showed better results as the additive amount of a polyhydric alcohol having a molecular weight of 100 or less increased. However, in the case where the additive amount of a polyhydric alcohol is too large, the osmotic pressure ratio of the preparation becomes higher.

Due to such a precipitation prevention effect of the present invention, in the production process of the preparation, the precipitation of Compound A on the wall surface of the preparation container at the time of preparing the preparation, or the precipitation of Compound A in the process of the filling machine can be suppressed. In the case where the precipitation of Compound A occurs, the content of Compound A in the preparation may decrease and the precipitated Compound A may become an insoluble foreign matter, so there is a risk of quality incompatibility. Due to suppression of precipitation in the present invention, it is possible to provide a liquid medicinal preparation which does not generate precipitates during the production process and is suitable for mass production.

The liquid medicinal preparation of the present invention is useful as an antitumor agent.

What is claimed is:
1. A liquid composition, comprising:
   1-(2-deoxy-2-fluoro-4-thio-β-D-arabinofuranosyl)cytosine or a salt thereof;
   a polyhydric alcohol having a molecular weight of 100 or less; and
   water,
   wherein the polyhydric alcohol is glycerin, propylene glycol, or butanediol.
2. The liquid composition according to claim 1, wherein the polyhydric alcohol is glycerin.

3. The liquid composition according to claim 1, wherein the content of the polyhydric alcohol is 0.5% to 10% by mass.

4. The liquid composition according to claim 1, wherein the content of the polyhydric alcohol is 0.5% to 5% by mass.

5. The liquid composition according to claim 1, wherein the preparation has a pH of 1.5 to 6.9.

6. The liquid composition according to claim 1, wherein the preparation has a pH of 2.0 to 4.0.

7. The liquid composition according to claim 1, wherein the content of 1-(2-deoxy-2-fluoro-4-thio-β-D-arabinofuranosyl)cytosine or a salt thereof is 1 to 50 mg/mL.

8. The liquid composition according to claim 1, wherein the salt of 1-(2-deoxy-2-fluoro-4-thio-β-D-arabinofuranosyl)cytosine is a methanesulfonate, hydrochloride, ½ sulfate, nitrate, or hydroiodide of 1-(2-deoxy-2-fluoro-4-thio-β-D-arabinofuranosyl)cytosine.

9. The liquid composition according to claim 1, which is an injectable solution injection.

* * * * *